(12) United States Patent
Amanatullah

(10) Patent No.: US 11,344,320 B2
(45) Date of Patent: May 31, 2022

(54) MODULAR TOTAL KNEE ARTHROPLASTY SYSTEM AND METHOD

(71) Applicant: Arthrology Consulting, LLC, Palo Alto, CA (US)

(72) Inventor: Derek Amanatullah, Palo Alto, CA (US)

(73) Assignee: Arthrology Consulting, LLC, Menlo Park, CA (US)

( * ) Notice: Subject to any disclaimer, the term of this patent is extended or adjusted under 35 U.S.C. 154(b) by 207 days.

(21) Appl. No.: 16/833,194

(22) Filed: Mar. 27, 2020

(65) Prior Publication Data

US 2020/0222063 A1   Jul. 16, 2020

Related U.S. Application Data

(63) Continuation of application No. 16/209,888, filed on Dec. 4, 2018, now Pat. No. 10,639,047, which is a
(Continued)

(51) Int. Cl.
| | |
|---|---|
| *A61B 17/16* | (2006.01) |
| *A61F 2/38* | (2006.01) |
| *A61F 2/46* | (2006.01) |
| *A61B 17/17* | (2006.01) |
| *A61F 2/30* | (2006.01) |

(52) U.S. Cl.
CPC ...... *A61B 17/1675* (2013.01); *A61B 17/1764* (2013.01); *A61F 2/389* (2013.01); *A61F 2/3859* (2013.01); *A61F 2/461* (2013.01); *A61F 2/4684* (2013.01); *A61F 2002/30205* (2013.01);
(Continued)

(58) Field of Classification Search
CPC ............ A61B 17/1675; A61B 17/1764; A61B 17/142; A61B 17/144; A61B 17/1615; A61B 17/92; A61B 17/921; A61F 2/389; A61F 2/46; A61F 2/4603; A61F 2/461; A61F 2/4619; A61F 2/4229
See application file for complete search history.

(56) References Cited

U.S. PATENT DOCUMENTS

| | | | |
|---|---|---|---|
| 3,835,858 A | * | 9/1974 | Hagen ................ A61B 17/1633 606/180 |
| 4,479,271 A | | 10/1984 | Bolesky et al. |

(Continued)

*Primary Examiner* — Brian A Dukert
(74) *Attorney, Agent, or Firm* — Knobbe, Martens, Olson & Bear, LLP

(57) ABSTRACT

A modular system for total knee arthroplasty includes a modular trial implant assembly. The modular implant assembly includes an elongate shaft configured for insertion into an elongate cavity in a bone, a reamer removably coupleable to the elongate shaft via a connection that allows the reamer to rotate while the elongate shaft remains in a substantially fixed angular orientation. The reamer has an outer surface that tapers toward the distal end configured to form a tapered cavity in an end of a bone in which the reamer is inserted and rotated. The modular trial implant assembly further includes a trial implant removably coupleable to a proximal end of the reamer. A modular final implant assembly includes an elongate stem, a tapered body and an implant body, each having a size and shape that can substantially correspond to a size and shape of the elongate shaft, the reamer and the trial implant, respectively.

21 Claims, 15 Drawing Sheets

Related U.S. Application Data continuation of application No. 15/477,578, filed on Apr. 3, 2017, now Pat. No. 10,182,830.

(60) Provisional application No. 62/318,684, filed on Apr. 5, 2016.

(52) U.S. Cl.
CPC ......... *A61F 2002/30616* (2013.01); *A61F 2002/30878* (2013.01); *A61F 2002/4619* (2013.01)

(56) References Cited

U.S. PATENT DOCUMENTS

| | | | |
|---|---|---|---|
| 4,936,853 A | 6/1990 | Fabian et al. | |
| 4,938,769 A | 7/1990 | Shaw | |
| 5,100,407 A | 3/1992 | Conrad et al. | |
| 5,257,995 A * | 11/1993 | Umber | A61B 17/8872 606/86 R |
| 5,290,313 A | 3/1994 | Heldreth | |
| 5,413,605 A | 5/1995 | Ashby et al. | |
| 6,139,581 A | 10/2000 | Engh et al. | |
| 6,146,424 A | 11/2000 | Gray, Jr. et al. | |
| 6,214,052 B1 | 4/2001 | Burkinshaw | |
| 6,447,549 B1 | 9/2002 | Taft | |
| 6,869,447 B2 | 3/2005 | Lee et al. | |
| 7,294,149 B2 | 11/2007 | Hozack et al. | |
| 7,618,451 B2 | 11/2009 | Berez et al. | |
| 7,727,281 B2 | 6/2010 | Ensign | |
| 7,935,118 B2 * | 5/2011 | Vendrely | A61B 17/17 606/87 |
| 8,366,782 B2 | 2/2013 | Wright | |
| 8,496,666 B2 | 7/2013 | Ries et al. | |
| 8,758,444 B2 | 6/2014 | Wentorf et al. | |
| 8,845,745 B2 | 9/2014 | Dees, Jr. et al. | |
| 9,101,476 B2 | 8/2015 | Deruntz et al. | |
| 9,603,720 B2 * | 3/2017 | Kelley | A61B 17/155 |
| 2009/0149963 A1 | 6/2009 | Sekel | |
| 2010/0217267 A1 | 8/2010 | Bergin | |
| 2011/0112540 A1 | 5/2011 | McLean et al. | |
| 2013/0123930 A1 * | 5/2013 | Burt | A61B 17/1684 623/19.14 |
| 2013/0289731 A1 | 10/2013 | Katerberg et al. | |

\* cited by examiner

MODULAR TOTAL KNEE ARTHROPLASTY SYSTEM AND METHOD

CROSS-REFERENCE TO RELATED APPLICATIONS

Any and all applications for which a foreign or domestic priority claim is identified in the Application Data Sheet as filed with the present application are hereby incorporated by reference under 37 CFR 1.57 and should be considered a part of this specification.

BACKGROUND

Field

The present invention relates to a system and method for knee replacement surgery and more particularly to a modular total knee arthroplasty system and method for use in primary and revision knee replacement.

Description of the Related Art

Total or partial knee replacement is very common, for example to treat conditions such as arthritis or treat injuries to the knee joint (e.g., from trauma, accidents, sport injuries, etc.). Total knee arthroplasty involves implanting a first prosthetic device on the distal end of the femur and a second prosthetic device on the proximal end of the tibia, where the first and second prosthetic devices replace the natural articulating bone surfaces of the knee joint (e.g., femoral condyles). Such surgical procedures involve cutting sections of the femur and tibia to accommodate the prosthetic devices in proper alignment, and can be complex and time consuming.

In some cases, it is necessary to perform a knee replacement revision surgery to replace the previously implanted knee prosthetic devices. For example, the previously implanted knee prosthetic devices may loosen over time, for example, from the production of wear debris, infection, or fracture. Revision surgery is typically more complicated and time consuming than an initial knee replacement surgery because the surgeon must remove the previously implanted device, which was cemented into the bone or has existing bone into the device. In addition, once the surgeon remove the implant, there is less bone remaining for fixation of the revision implant.

SUMMARY

In accordance with one aspect of the invention, an improved total knee arthroplasty system and method is provided that simplifies the process of delivering a primary or revision knee replacement implant, as well as to replace an existing knee replacement implant, and makes such processes less time consuming.

In accordance with one aspect, a modular system for total knee arthroplasty is provided. The system comprises a modular trial implant assembly. The modular implant assembly comprises an elongate shaft configured for insertion into an elongate cavity in a bone. The modular trial implant assembly also comprises a reamer that extends between a proximal end and a distal end, the reamer being removably coupleable to a proximal end of the elongate shaft via a connection that allows the reamer to rotate while the elongate shaft remains in a substantially fixed angular orientation. The reamer has an outer surface that tapers toward the distal end of the reamer. The outer surface further has a plurality milling elements extending between the proximal and distal ends of the reamer about the circumference of the reamer, the milling elements configured to form a tapered cavity in an end of a bone in which the reamer is inserted and rotated. The modular trial implant assembly further comprises a trial implant removably coupleable to a proximal end of the reamer. The elongate shaft is configured to provide angular orientation but not rotational stability when inserted into the elongate cavity, and wherein the reamer is configured to provide rotational and axial stability in the tapered cavity.

In accordance with another aspect, a modular system for total knee arthroplasty is provided. The system comprises a modular trial implant assembly. The modular implant assembly comprises an elongate shaft configured for insertion into an elongate cavity in a bone. The modular trial implant assembly also comprises a reamer that extends between a proximal end and a distal end, the reamer being removably coupleable to a proximal end of the elongate shaft via a connection that allows the reamer to rotate while the elongate shaft remains in a substantially fixed angular orientation. The reamer has an outer surface that tapers toward the distal end. The reamer comprises a plurality of sequentially nestable portions releasably coupleable with each other to define a tapered shape, where a maximum outer diameter of the tapered shape is defined by the last of the sequentially nestable portions that are coupled to each other. The plurality of sequentially nestable portions are configured to rotate as a single unit when assembled together. The outer surface further has a plurality milling elements extending between the proximal and distal ends of the reamer about the circumference of the reamer, the milling elements configured to form a tapered cavity in an end of a bone in which the reamer is inserted and rotated. The modular trial implant assembly further comprises a trial implant removably coupleable to a proximal end of the reamer. The elongate shaft is configured to provide angular orientation but not rotational stability when inserted into the elongate cavity, and wherein the reamer is configured to provide rotational and axial stability in the tapered cavity.

In accordance with another aspect, a modular kit for total knee arthroplasty is provided. The kit comprises a plurality of elongate shafts configured for insertion into an elongate cavity in a femur or tibia bone, each of the elongate shafts differing in one or both of length and outer diameter. The kit also comprises a plurality of tapered reamers differing in one or both of length and maximum outer diameter, the reamer having an outer surface with a plurality milling elements extending about the circumference of the reamer. The kit also comprises a plurality of trial implants of different sizes, wherein each of the trial implants is coupleable to a proximal end of each of the tapered reamers, which is coupleable to a proximal end of each of the elongate shafts to assemble a trial implant assembly.

In accordance with another aspect, the modular kit further comprises a plurality of elongate stems configured for insertion into an elongate cavity in a femur or tibia bone, each of the elongate shafts differing in one or both of length and outer diameter, a plurality of tapered cone bodies differing in one or both of length and maximum outer diameter and a plurality of implants of different sizes. Each of the implants is coupleable to a proximal end of each of the tapered cone bodies, which is coupleable to a proximal end of each of the elongate stems to assemble a final implant assembly. Optionally, the plurality of elongate stems, plurality of tapered cone bodies and plurality of implants substantially correspond in size and shape with the plurality of elongate shafts, plurality of tapered reamers and plurality of trial implants, respectively. Optionally, at least one of the plurality of tapered cone bodies has an outer surface with a plurality of flute elements extending about the circumference of the tapered conical body to define a tapered fluted conical body. Optionally, at least one of the plurality of tapered cone bodies has an outer surface that is porous. Optionally, at least one of the plurality of tapered cone bodies has an outer surface that is rough.

DETAILED DESCRIPTION

Figure 1:
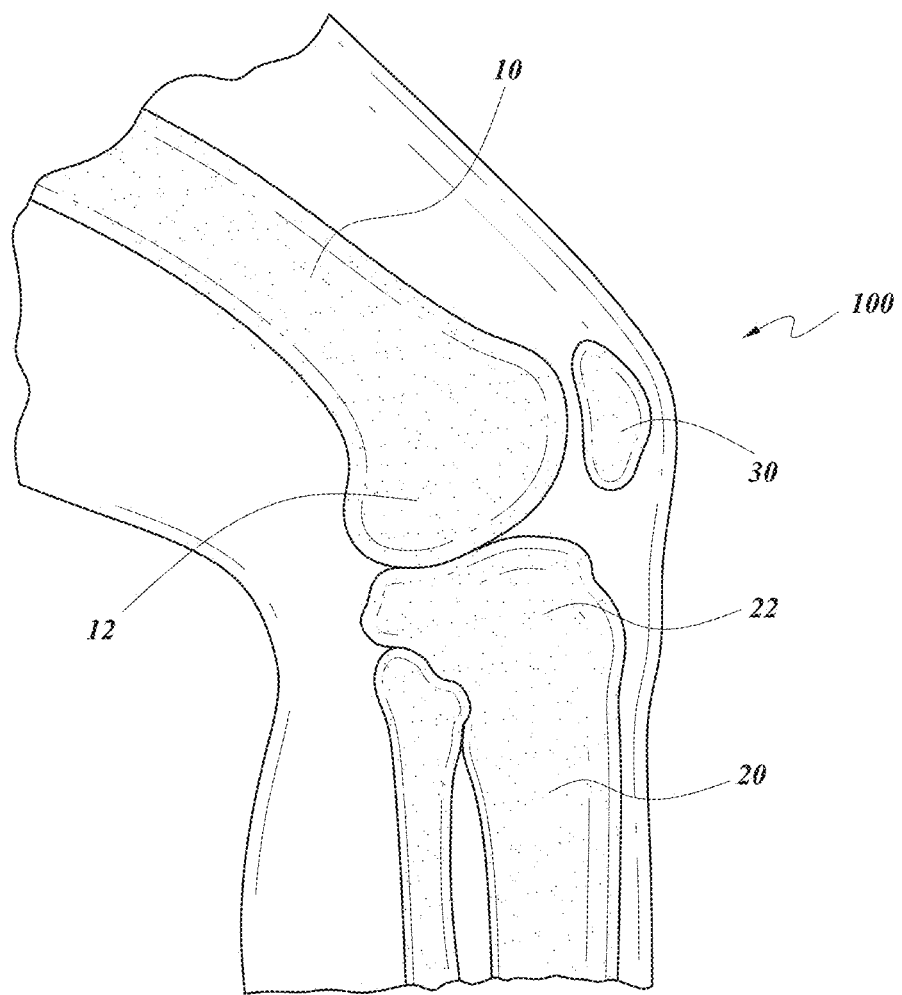
FIG. 1 is a schematic view of a side view of a knee joint.
Figure 2:
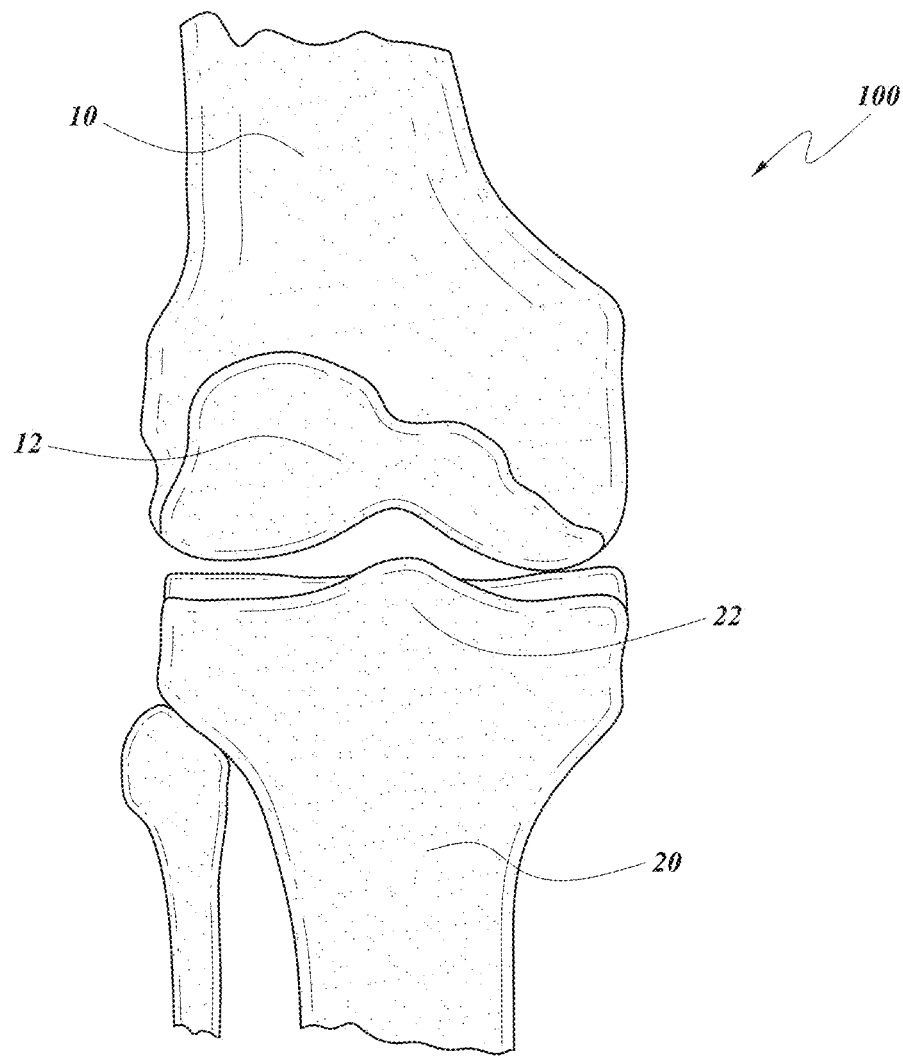
FIG. 2 is a schematic view of a front view of a knee joint.

FIGS. 1-2 shows a schematic side and front view, respectively of a human knee joint 100, which includes a distal end 12 of a femur 10, a proximal end 22 of a tibia 20, and a patella 30. Total knee arthroplasty (TKA) involves removal of at least a portion of the distal end 12 of the femur 10 and at least a portion of the proximal end 22 of the tibia 20 and implantation of prosthetic femoral and tibial components, as described further below.

Figure 3:
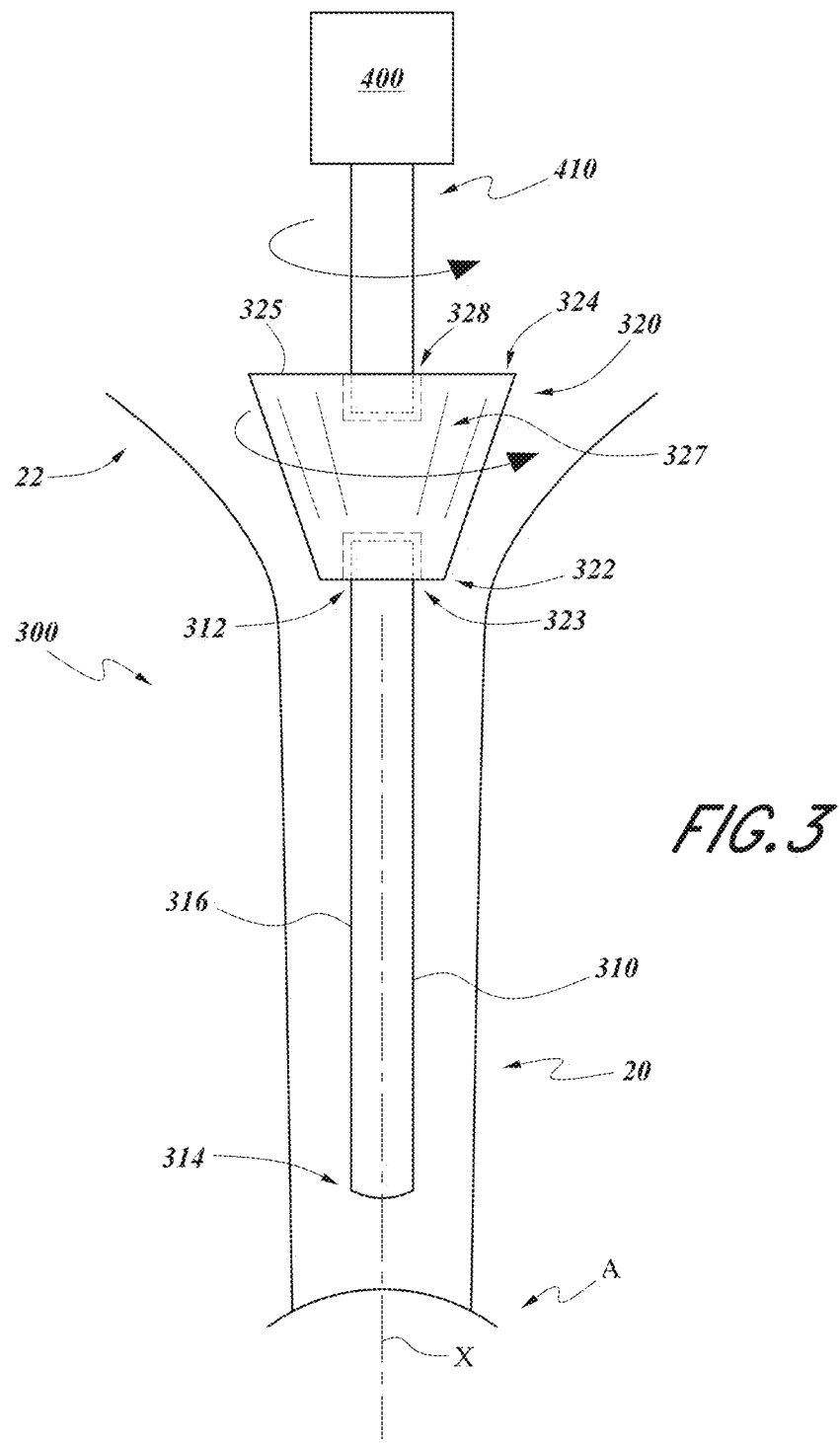
FIG. 3 is a schematic side view of one embodiment of a reaming assembly.

FIG. 3 shows one embodiment of an assembly 300 that can be used during a total knee replacement or total knee revision surgical procedure, as further discussed below. The assembly 300 can include an elongate shaft or stem 310 that can be inserted into the bone. In the illustrated embodiment, the assembly 300 is schematically shown disposed in the tibia 20. However, the assembly 300 can also be used in femur 10. The elongate shaft 310 extends between a proximal end 312 and a distal end 314 and has an outer surface 316. Optionally, the elongate shaft 310 can be cylindrical in shape (e.g., have a circular transverse cross-section), conical (e.g., circular in transverse cross-section but with decreasing cross-sectional area as to crease a taper in the orthogonal plane), or splined/fluted (e.g., have a star-like transverse cross-section). The outer surface 316 can optionally be a smooth surface. As used herein, "smooth" is intended to have its ordinary meaning (e.g., free from perceptible projections, lumps or indentations); in connection with orthopedic components, "smooth" is meant to refer, for example, to a surface that is not fluted or has ridges protruding from it, so the component does not provide rotational stability. In the illustrated embodiment, the elongate shaft 310 extends along an axis X that generally coincides with (e.g., is parallel to, is coaxial with) a central axis of the tibia 20 (e.g., where the tibia 20 extends in a normally linear manner such that the axis X of the elongate shaft 310 intersects a transverse plane at an ankle A at the distal end of the tibia 20 substantially at a 90 degree angle). With respect to the femoral implant, elongate shaft 310 extends along an axis X that generally coincides with (e.g., is parallel to, is coaxial with) a central axis of the femur 10 (e.g., where the femur 10 extends in a normally linear manner such that the axis X of the elongate shaft 310 intersects a transverse plane at a hip at the proximal end of the femur 10 substantially at a 90 degree angle). In one embodiment, the elongate shaft or stem 310 is substantially fixed within the bone (e.g., within the tibia 20) so that it does not rotate within the bone during the procedure. Optionally, the elongate shaft 310 can have a length of between about 25 mm and about 200 mm and a diameter of between about 10 mm and about 30 mm. However, the elongate shaft 310 can have other suitable dimensions. The elongate shaft 310 can define a majority (e.g., greater than 50%, greater than 60%, greater than 75%, greater than 80%, etc.) of the length of the assembly 300.

With continued reference to FIG. 3, the proximal end 312 of the elongate shaft 310 can removably couple with a reamer component 320, optionally via a bearing connection 323 (e.g., rolling element bearing, such as one with an inner race that couples with the proximal end 312 of the elongate shaft 310 and an outer race that couples with the reamer 320, where the inner and outer races rotate relative to each other). In another embodiment, the connection 323 can be a boss that allows rotational movement between the reamer component 320 and the elongate shaft 310, so that the reamer 320 can rotate while the elongate shaft 310 remains in a substantially fixed angular orientation. In one embodiment, the proximal end 312 of the elongate shaft 310 can have a cross-sectional shape (e.g., hexagonal, pentagonal, square) that substantially matches a shape of an opening in the bearing connection that receives the proximal end 312. Accordingly, the reamer 320 can rotate without rotating the elongate shaft 310. The reamer 320 can extend between a proximal end 324 and a distal end 322. In the illustrated embodiment, the reamer 320 has a tapered cone shape so that the outer surface 326 of the reamer 320 tapers from the proximal end 324 toward the distal end 322. The outer surface 326 of the reamer 320 can have one or more milling elements 327 (e.g., ridges) that allow the reamer 320 to create a cavity in the bone having a corresponding shape as the reamer 320. In the illustrated embodiment, the tapered cone shaped reamer 320 can be rotated to form a tapered cone shaped cavity in the proximal end 22 of the tibia 20.

The proximal end 324 of the reamer 320 can have a connector 328 shaped to couple with a corresponding end of a shaft 410 that can be chucked to an orthopedic tool (manual or electric), such as a drill 400. In one embodiment, the connector 328 is a female connector having an opening shaped (e.g., with a cross-sectional shape that is square, hexagonal, pentagonal, etc.) to receive a similarly shaped end of the shaft 410. In another embodiment, the connector 328 is a male connector having a cross-sectional shape (e.g., square, hexagonal, pentagonal, etc.) corresponding to a shape of an opening in the shaft 410 that receives the connector 328. Once chucked to the drill 400, the shaft 410 can be rotated, which can in turn rotate the reamer 320 via the connector 328 to form the cavity in the bone without rotating the elongate shaft 310, which remains in a fixed orientation in the bone.

Figure 4:
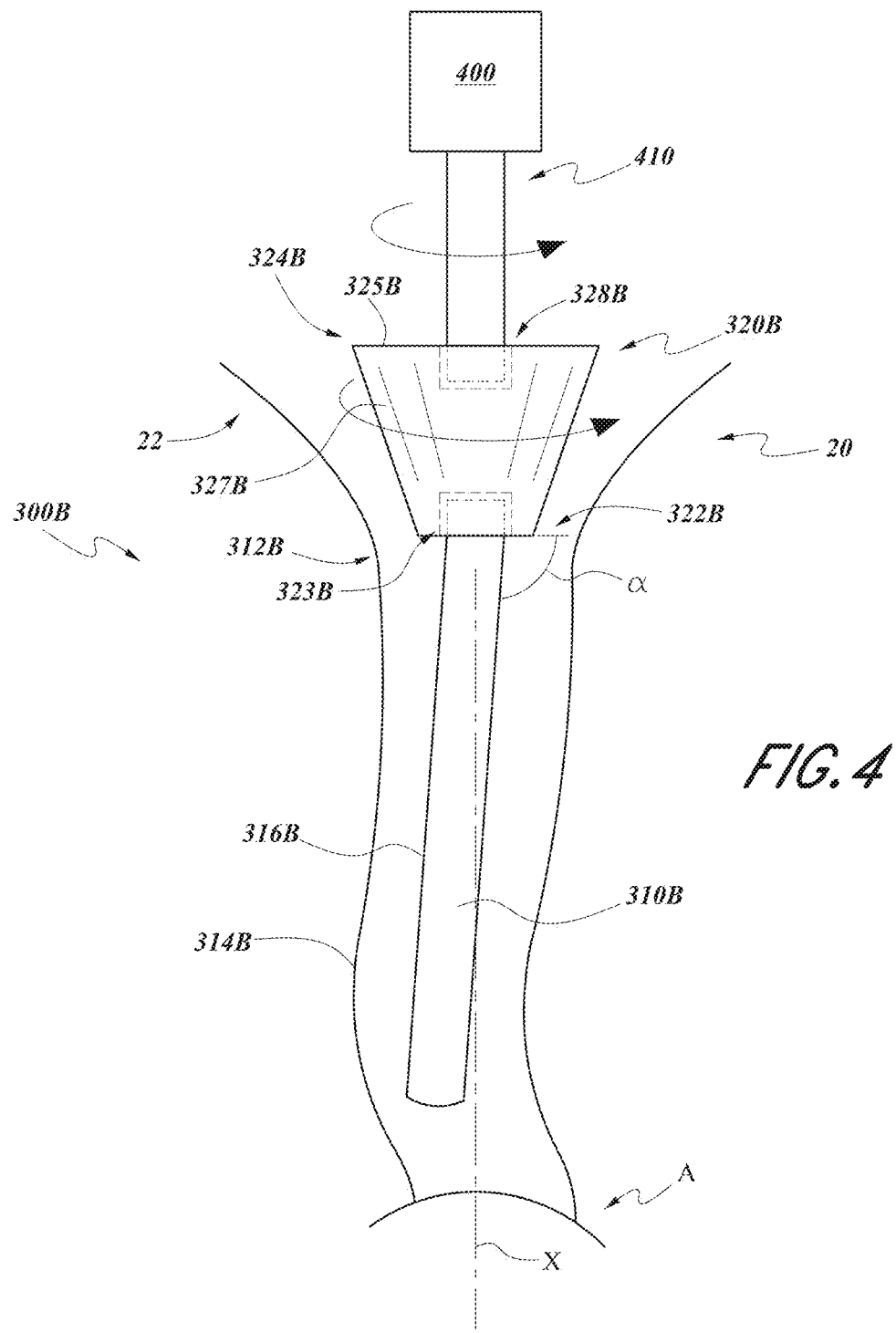
FIG. 4 is a schematic side view of another embodiment of a reaming assembly.

FIG. 4 shows an embodiment of an assembly 300B that is similar to the assembly 300 in FIG. 3, except as described below. The assembly 300B is constructed similar to the assembly 300 shown in FIG. 3, except as noted below. Therefore, the references numerals used to designate the various components of the assembly 300B are identical to those used for identifying the corresponding components of the assembly 300 in FIG. 3, except that a "B" has been added to the reference numerals.

In the illustrated embodiment, the elongate shaft or stem 310B extends at an angle α relative to an axis of the femur 10 or tibia 20 (e.g., relative to a central axis X of the bone), where the bone (e.g., tibia) is s-shaped or to account for normal anatomy of the distal femur including variations of the anatomic axis in the coronal plane and femoral bow in the sagittal plane. In one embodiment the angle α can be between about 3 degrees and about 5 degrees. In other embodiments, the angle α can have other values, such as between about 1 degree and about 12 degrees. The proximal end 312B of the elongate shaft 310B extends along a vertical axis, while the portion of the elongate shaft 310B distal of the proximal end 312B extends at said offset angle α relative to the vertical axis X. As with the assembly 300, the assembly 300B has a reamer 320B that removably couples to the proximal end 312B of the elongate shaft 310B via a rotatable connection 323B (e.g., a bearing connection, such as rolling element bearing, a boss, etc.) that allows the elongate shaft 310B to remain in a fixed orientation while the reamer 320B is rotated to ream a cavity into the end of the bone (e.g., the proximal end 22 of the tibia 20). The reamer 320B is similar to the reamer 320 and operates in the same manner, can have a tapered cone shape, and can be coupled to a drill 400 via a shaft 410 that can be chucked to the drill 400 and that can couple to a connector 328B in the proximal end 324B of the reamer 320.

Figure 5A:
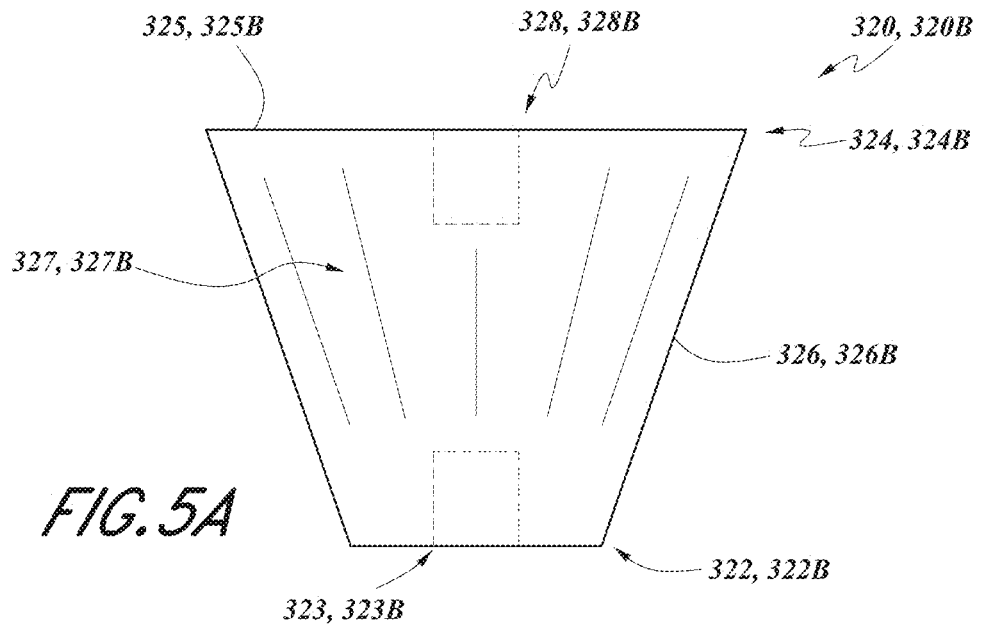
FIG. 5A is a schematic side view of one embodiment of a reaming cone.
Figure 5B:
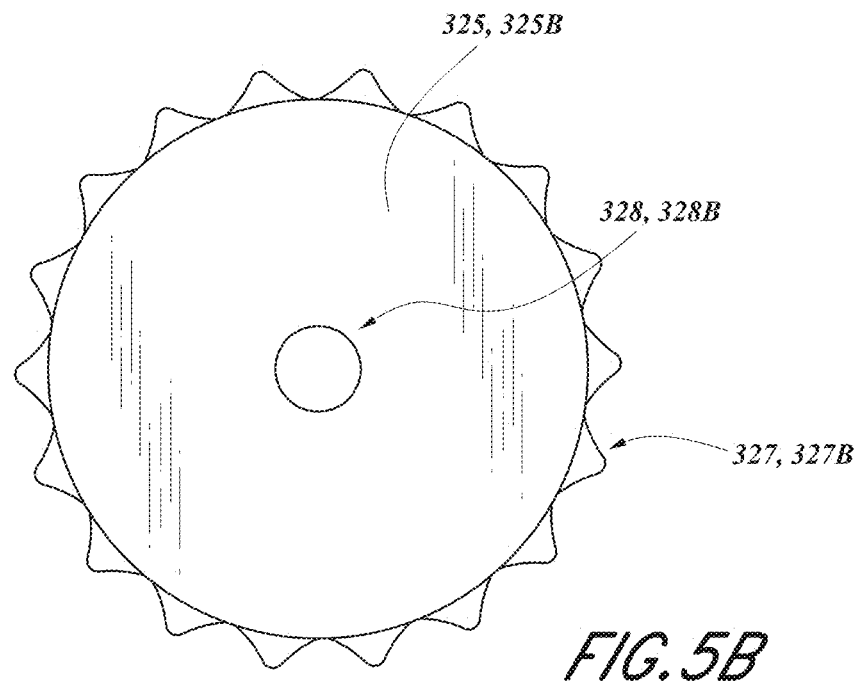
FIG. 5B is a schematic top view of the reaming cone of FIG. 5A.

FIGS. 5A and 5B show a schematic side view and top view of the reamer 320, 320B shown in FIGS. 3-4. The proximal end 324, 324B of the reamer 320, 320B can have a surface 325, 325B that in one embodiment is generally planar. In other embodiments, the surface 325, 325B can have other suitable shapes, such as concave, convex, etc. The connector 328, 328B at the proximal end 324, 324B of the reamer 320, 320B in FIG. 5B can be female and have a generally circular shape (e.g., a cylindrical recess) that receives the shaft 410. In other embodiments, the connector 328, 328B can have other shapes (e.g., square, pentagonal, hexagonal) that mates with a similarly shaped end of the shaft 410 to allow rotation of the shaft 410 (e.g., via the drill 400) to cause rotation of the reamer 320, 320B. In the illustrated embodiment, the proximal end 324, 324B and the distal end 322, 322B of the reamer 320, 320B can extend along substantially parallel planes, with the outer diameter of the proximal end 324, 324B being greater than the outer diameter of the distal end 322, 322B to thereby define the tapered cone shape.

Figure 6A:
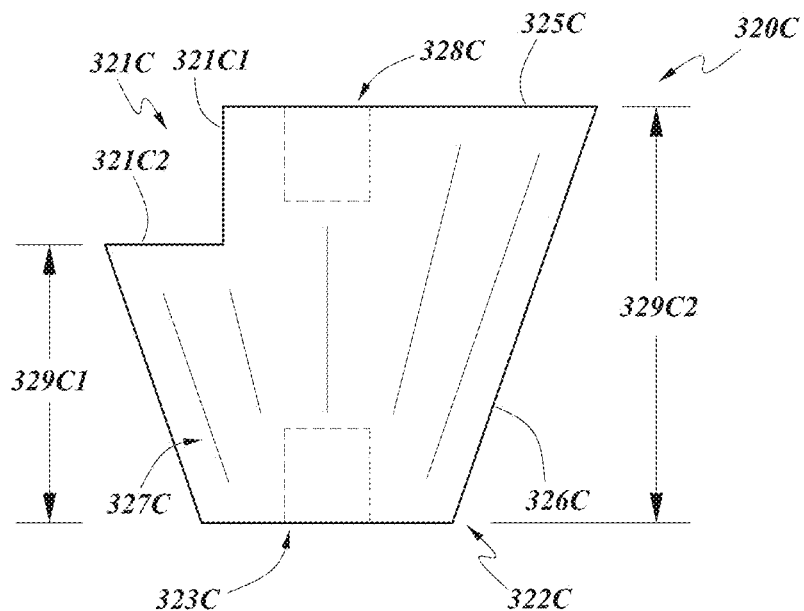
FIG. 6A is a schematic side view of another embodiment of a reaming cone.
Figure 6B:
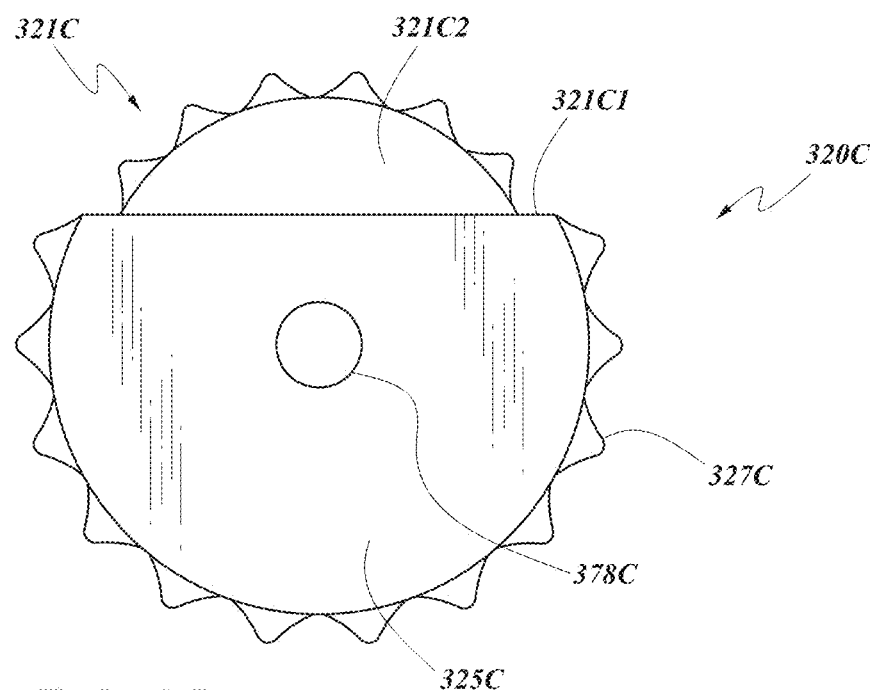
FIG. 6B is a schematic top view of the reaming cone of FIG. 6A

FIGS. 6A-6B show an embodiment of a reamer 320C that is similar to the reamer 320, 320B in FIGS. 5A-5B, except as described below. The reamer 320C is constructed similar to the reamer 320, 320B shown in FIGS. 5A-5B, except as noted below. Therefore, the references numerals used to designate the various features of the reamer 320C are identical to those used for identifying the corresponding features of the reamer 320, 320B in FIGS. 5A-5B, except that a "C" has been added to the reference numerals.

In the illustrated embodiment, a proximal end 324C of the reamer 320C has a cutout 321C so that the shape of the reamer 320C is not a complete tapered cone. The cutout 321C defines a vertical surface 321C1 and a horizontal surface 321C2 that are optionally substantially perpendicular to each other. The reamer 320C has a height 329C1 between the distal end 322C and the horizontal surface 321C2 of the cutout 321C. The reamer 320C has a height 329C2 between the distal end 322C and the proximal end 324C. In one embodiment, the height 329C1 can be approximately one half the height 329C2. However, in other embodiments the ratio between the height 329C1 and the height 329C2 can have other suitable values (e.g., $1/4^{th}$, $1/3^{rd}$, $3/4^{th}$, etc.). The cutout 321C in the reamer 320C allows the reamer 320C to accommodate (e.g., to not impinge on) the implant (e.g., the femoral knee implant) when implant is coupled to the reamer 320C component, as further discussed below. The reamer 320C is otherwise similar to the reamer 320, 320B and operates in the same manner, can have a generally tapered cone shape, and can be coupled to a drill 400 via a shaft 410 that can be chucked to the drill 400 and that can couple to a connector 328C in the proximal end 324C of the reamer 320C. The distal end 322C of the reamer can couple to a proximal end 312, 312B of an elongate shaft or stem 310, 310B via a rotatable connector 323, 323B (e.g., a bearing connector, boss, etc.) that allows the reamer 320C to rotate (e.g., to create the tapered cavity in the femur) while the shaft 310, 310B remains in a fixed orientation (e.g., the elongate shaft 310, 310B does not rotate with the reamer 320C).

Figure 7:
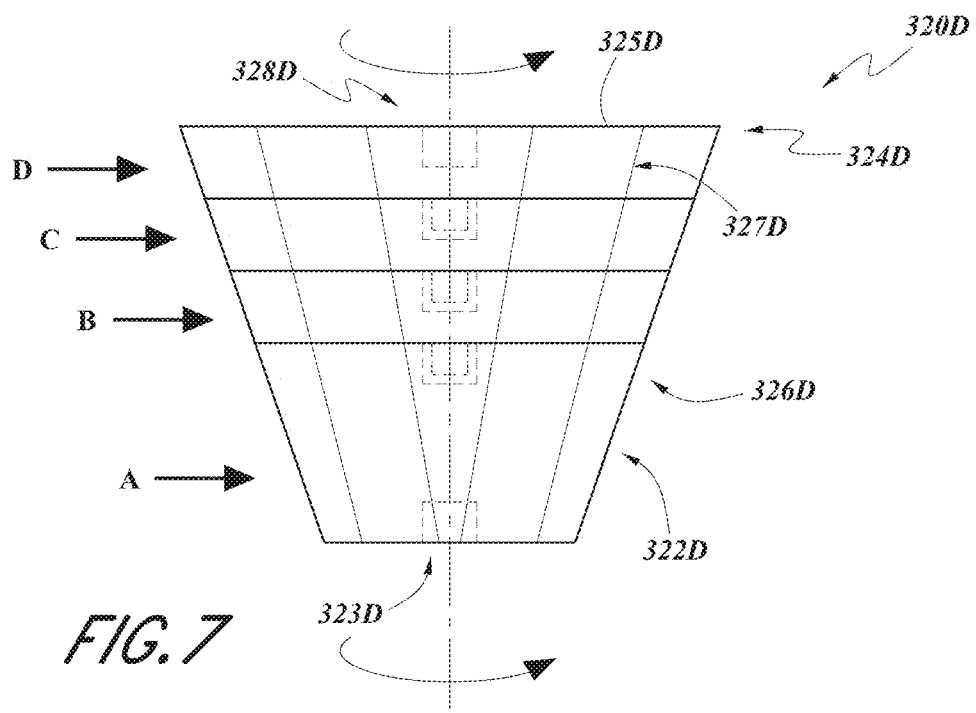
FIG. 7 is a schematic side view of another embodiment of a reaming cone.

FIG. 7 shows an embodiment of a reamer 320D that is similar to the reamer 320, 320B in FIGS. 3-5B, except as described below. The reamer 320D is constructed similar to the reamer 320, 320B shown in FIGS. 3-5B, except as noted below. Therefore, the references numerals used to designate the various features of the reamer 320D are identical to those used for identifying the corresponding features of the reamer 320, 320B in FIGS. 3-5B, except that a "D" has been added to the reference numerals.

In the illustrated embodiment, the reamer 320D can include one or more nested reamer portions A-D that can be sequentially coupled to each other to define the reamer body 320D. Though FIG. 7 shows the reamer 320D with four reamer portions A-D, one of skill in the art will recognize that the reamer 320D can have any number of reamer portions A-D, where at least a subset of the plurality of reamer portions A-D can be fixedly coupled to each other to define the reamer 320D body. The distal reamer portion A can have a rotatable coupling 323D (e.g., a bearing connection, such as a rolling element bearing, a boss, etc.) at the distal end 322D that can engage an elongate element, such as the elongate element 310, 310B in FIGS. 3-4. Each of the plurality of reamer portions A-D can have a connector (e.g., female coupling) 328D at its proximal end, which can receive a similarly shaped end of the shaft 410 that can be chucked to a driving element (e.g., a drill). Each of the reamer portions A-D can have a tapered cone outer surface 326D so that when two or more of the reamer portions A-D are sequentially nested, the outer surface of the reamer 320D defines a tapered cone surface. Each of the reamer portions A-D can also have milling elements 327D (e.g., ridges, edges) that align with each other when two or more of the plurality of reamer portions A-D are sequentially stacked together.

The plurality of reamer portions A-D advantageously fixedly couple to each other so that when two or more of the plurality of reamer portions A-D are nested together to define the reamer 320D structure they move as one piece (e.g., they rotate together). For example, the plurality of reamer portions A-D can each have one or more pins at a distal end that extend into one or more holes in a proximal end of an adjacent reamer portion. In another embodiment, each of the reamer portions A-D can each have one or more holes at a distal end that receive corresponding one or more pins in a proximal end of an adjacent reamer portion.

In use, the orthopedic surgeon could begin by using a first reamer portion (e.g., reamer portion A) to ream a cavity in a bone (e.g., in the proximal end 22 of the tibia 20). If the surgeon determined that a cavity needed to be larger, the surgeon could couple a second reamer portion (e.g., reamer portion B) onto the proximal end of the previously used reamer portion A to increase the size of the reamer 320D, and operate the reamer 320D (e.g., via a drill that operatively drives the reamer 320D) to create the larger cavity size. The surgeon could continue the process of nesting additional reamer portions onto the previously delivered reamer portions A-B, to create a cavity of the desired size in the bone.

Figure 8:
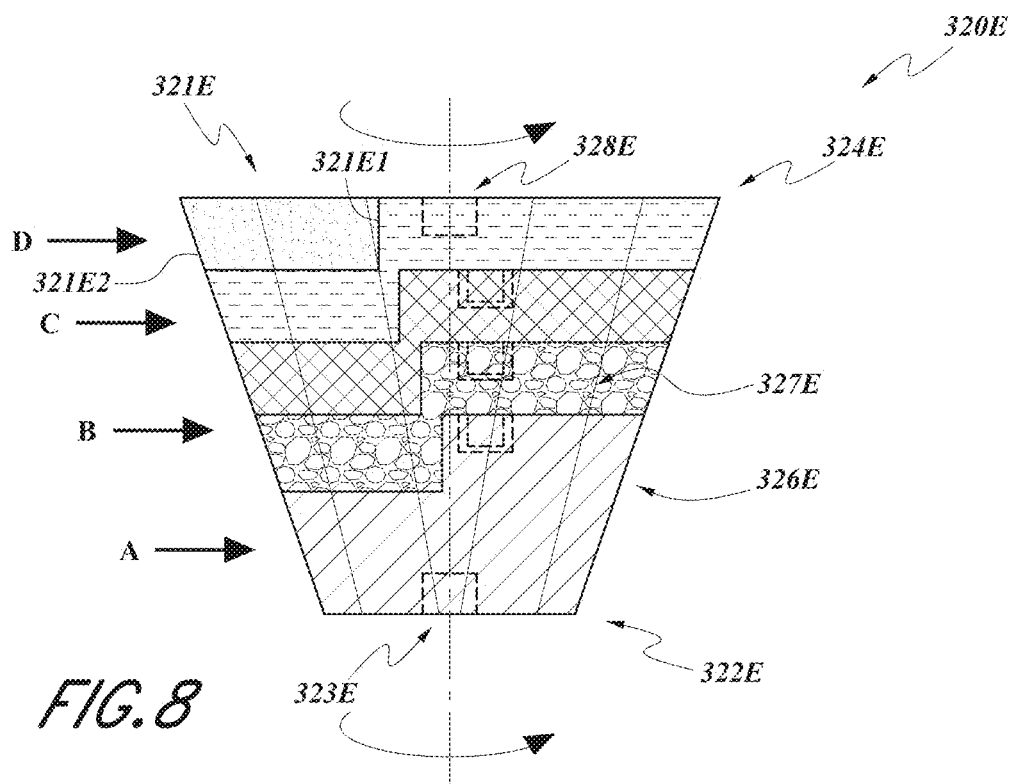
FIG. 8 is a schematic side view of another embodiment of a reaming cone.

FIG. 8 shows an embodiment of a reamer 320E that is similar to the reamer 320C, in FIGS. 6A-6B, except as described below. The reamer 320E is constructed similar to the reamer 320C shown in FIGS. 6A-6B, except as noted below. Therefore, the references numerals used to designate the various features of the reamer 320E are identical to those used for identifying the corresponding features of the reamer 320C in FIGS. 6A-6B, except that an "E" has been added to the reference numerals. FIG. 8 shows a reamer 320E that has a tapered cone shape from the proximal end to the distal end. Once the drill 400 is disconnected from the reamer 320E, a top segment of the proximal end can be removed to define the tapered cone with the cutout 321E. Additionally, the top segment can be textured or colored, so the user can see where the cut-out is on each cut-out cone reamer.

In the illustrated embodiment, the reamer 320E can include one or more nested reamer portions A'-D', each having a proximal cutout portion A1'-D1' that can be sequentially coupled to each other to define the reamer body 320E with a proximal cutout 321E. Though FIG. 8 shows the reamer 320E with four reamer portions A'-D', one of skill in the art will recognize that the reamer 320E can have any number of reamer portions A'-D', where at least a subset of the plurality of reamer portions A'-D' can be fixedly coupled to each other to define the reamer 320E body. The distal reamer portion A' can have a rotatable coupling 323E (e.g., a bearing connection, such as a rolling element bearing, a boss, etc.) at the distal end 322E that can engage an elongate element, such as the elongate element 310, 310B in FIGS. 3-4. Each of the plurality of reamer portions A'-D' can have a connector (e.g., female coupling) 328E at its proximal end, which can receive a similarly shaped end of the shaft 410 that can be chucked to a driving element (e.g., a drill). Each of the reamer portions A'-D' can define a portion of a tapered cone outer surface 326E (except where the reamer portion A'-D' has the cutout) so that when two or more of the reamer portions A'-D' are sequentially nested, the outer surface of the reamer 320E defines a tapered cone surface with a proximal cutout. Each of the reamer portions A'-D' can also have milling elements 327e (e.g., ridges, edges) that align with each other when two or more of the plurality of reamer portions A'-D' are sequentially stacked together.

The plurality of reamer portions A'-D' advantageously fixedly couple to each other so that when two or more of the plurality of reamer portions A'-D' are nested together to define the reamer 320E structure they move as one piece (e.g., they rotate together). For example, the plurality of reamer portions A'-D' can each have one or more pins at a distal end that extend into one or more holes in a proximal end of an adjacent reamer portion. In another embodiment, each of the reamer portions A'-D' can each have one or more holes at a distal end that receive corresponding one or more pins in a proximal end of an adjacent reamer portion.

In use, the orthopedic surgeon could begin by using a first reamer portion (e.g., reamer portion A') to ream a cavity in a bone (e.g., in the distal end 12 of the femur 10). If the surgeon determined that a cavity needed to be larger, the surgeon could couple a second reamer portion (e.g., reamer portion B') onto the proximal end of the previously used reamer portion A' to increase the size of the reamer 320E, and operate the reamer 320E (e.g., via a drill that operatively drives the reamer 320E) to create the larger cavity size. The surgeon could continue the process of nesting additional reamer portions onto the previously delivered reamer portions A'-B', to create a cavity of the desired size in the bone.

As with the reamer 320C, the cutout 321E of the reamer 320E allows it to accommodate (e.g., to not impinge on) the implant (e.g., the femoral knee implant) when implant is coupled to the reamer 320E component.

Figure 9:
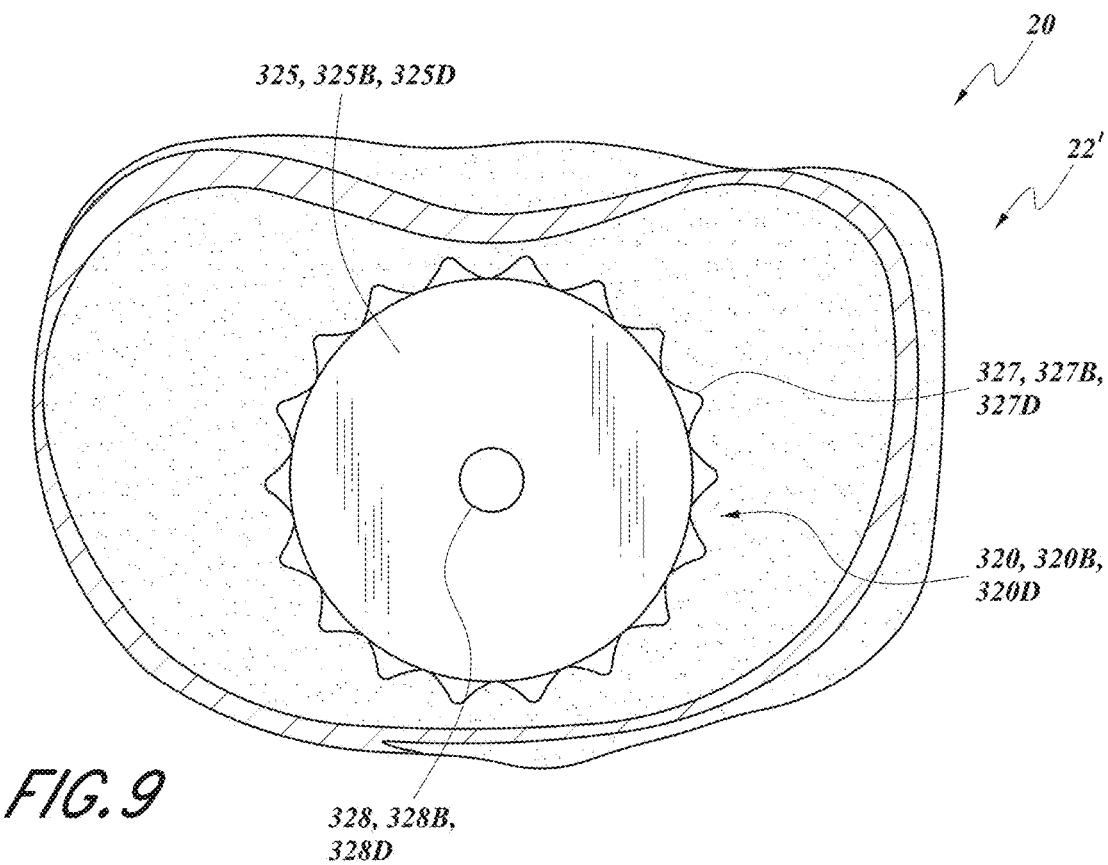
FIG. 9 is a schematic proximal end view of a cut tibia bone with a reaming cone therein.

FIG. 9 is an end view of a cut proximal end 22' of the tibia 20 into which the reamer 320, 320B, 320D has been inserted. In one embodiment, the proximal end 324, 324B, 324D of the reamer 320, 320B, 320D can be generally flush with the proximal surface of the cut tibia 20. Advantageously, the outer perimeter O of the reamer 320, 320B, 320D is generally circular and bounded by an outer boundary of cut proximal end 22' of the tibia 20.

Figure 10:
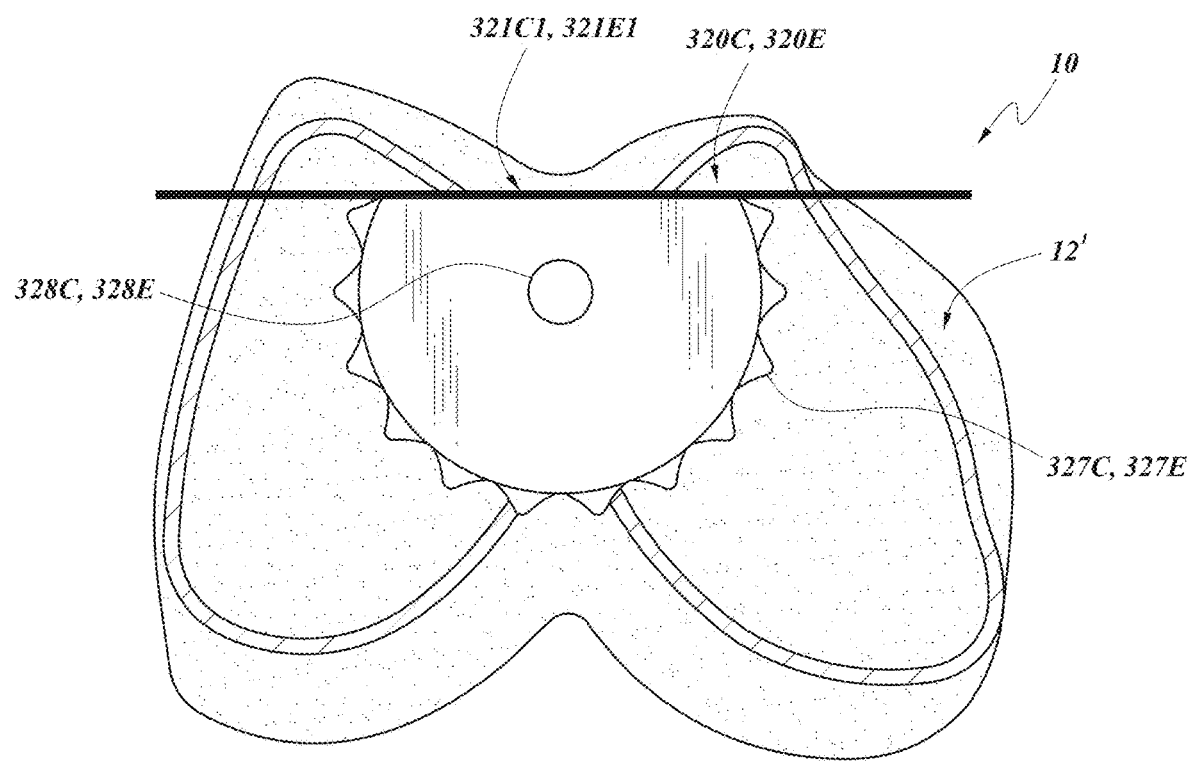
FIG. 10 is a schematic distal end view of a cut femur bone with a reaming cone therein.

FIG. 10 is an end view of a cut distal end 12' of the femur 10 into which the reamer 320C, 320E has been inserted. In one embodiment, the proximal end 324C, 324E of the reamer 320C, 320E can be generally flush with the distal surface 12' of the cut femur 10. Advantageously, the outer perimeter O of the reamer 320C, 320E is generally bounded by an outer boundary of cut distal end 12' of the tibia 20. In the illustrated embodiment, the vertical surface 321C1 of the cutout 321C, 321E faces the anterior side of the distal end 12 of the femur 10.

Figure 11A:
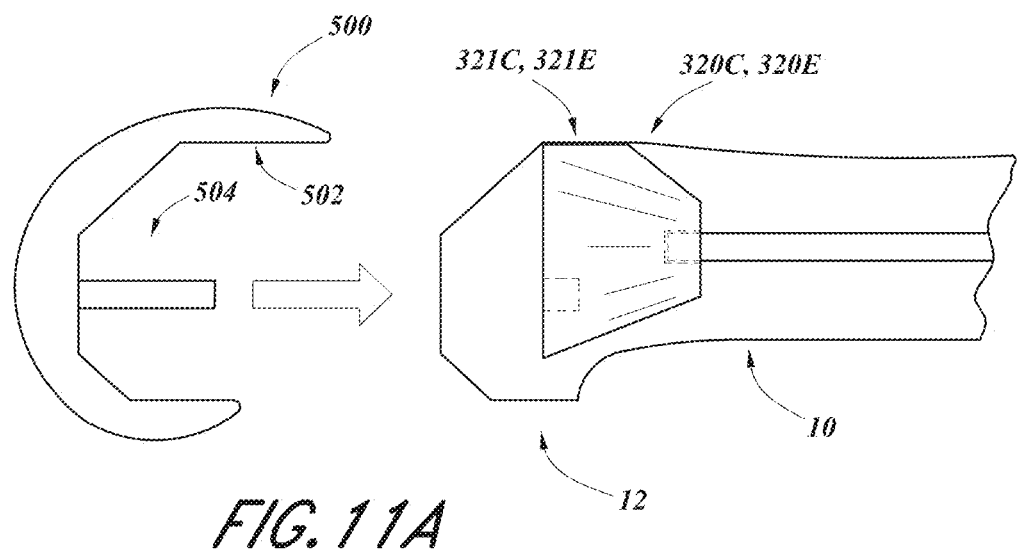
FIG. 11A is a schematic side view of a cut distal end of the femur bone with the reaming cone therein prior to installation of a trial femoral knee implant.
Figure 11B:
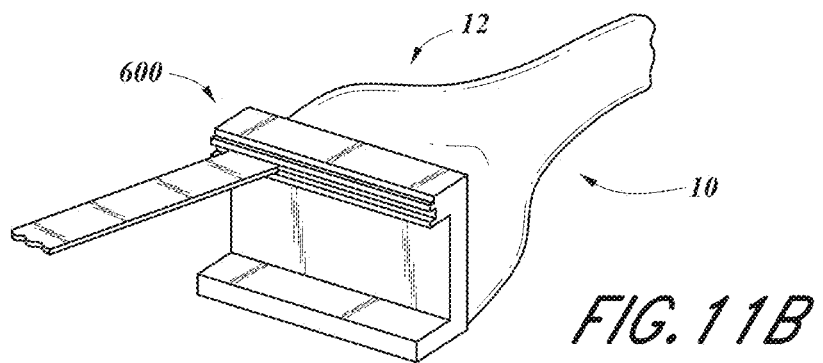
FIG. 11B is a schematic side view of a cutting guide disposed at the distal end of the femur to cut one or more planar surfaces to accommodate an implant.
Figure 12:
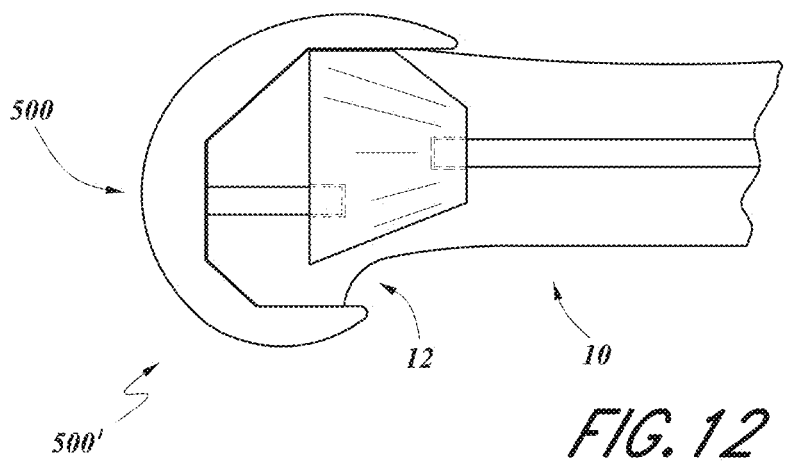
FIG. 12 is a schematic side view of the assembly in FIG. 12 after installation of the trial femoral knee implant.

FIG. 11A shows a schematic exploded view of a distal end 12 of the femur 10 with the reamer 320C, 320E inserted therein, prior to attachment of a trial implant 500 on the distal end 12. Once the reamer 320C, 320E has been inserted into the distal end 12 of the femur to form the desired cavity (e.g., conical cavity), a cutting guide 600 (see FIG. 11B) can be attached to the proximal end 324C, 324E of the reamer 320C, 320E to cut the femur 10 flush with one or more surfaces of the reamer 320C, 320E. The trial implant 500 can then be attached to the reamer 320C, 320E to define the trial implant assembly 500', as shown in FIG. 12. The trial implant 500' can be coupled with the reamer 320C, 320E in any suitable manner (e.g., with bone cement, with one or more screws, with a spline or other mechanical attachment, slot-key connection, tapered connection, etc.). Advantageously, as seen in FIGS. 11A, 12, the cut out portion 321C, 321E of the reamer 320C, 320E allows the trial implant 500 to be coupled with the proximal end 324C, 324E of the reamer 320C, 320E without impinging on the trial implant 500.

Figure 13:
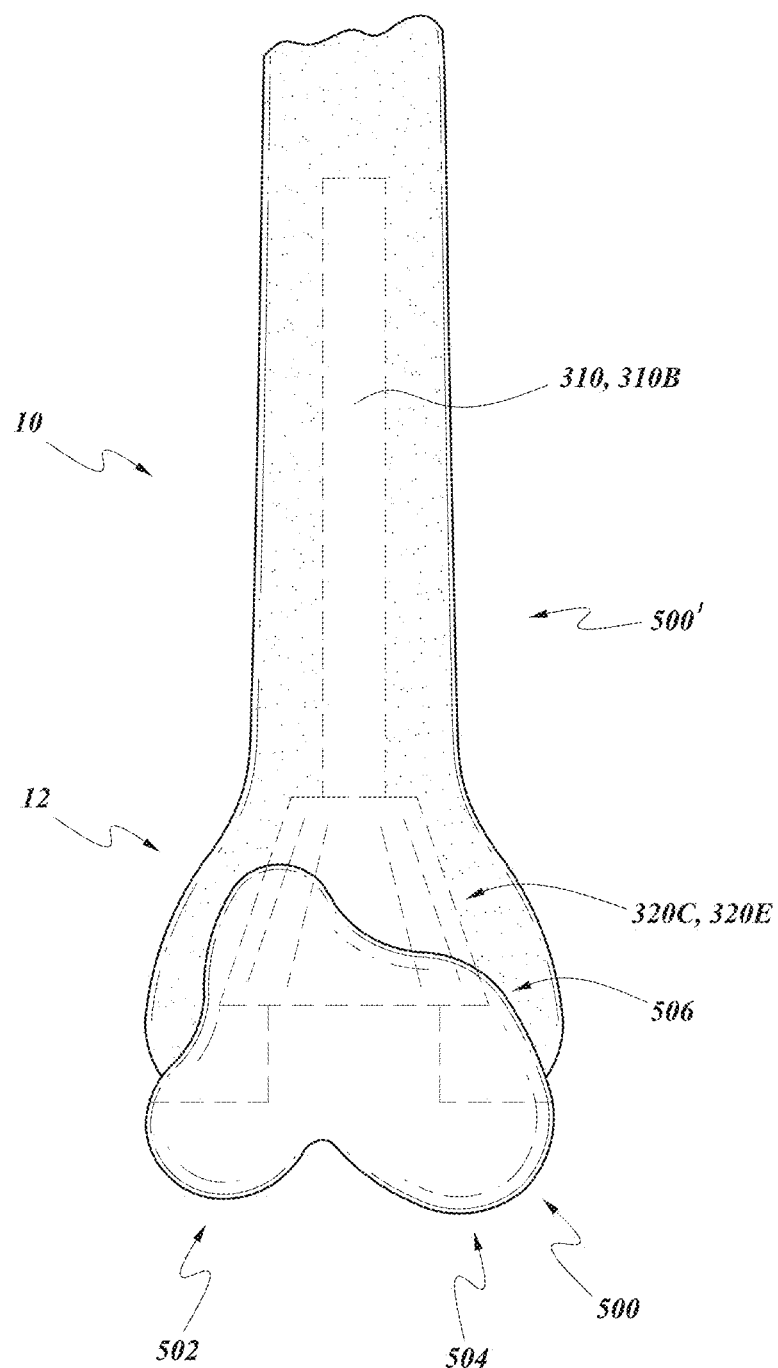
FIG. 13 if a front view of the assembly in FIG. 12 after installation of the trial femoral knee implant.

FIG. 13 shows a schematic front view of the distal end 12 of the femur 10 with the trial implant assembly 500', which includes the trial implant 500, the reamer 320C, 320E and the elongate shaft or stem 310, 310B. The trial implant 500 for the femur 10 can define a pair of condyle surfaces 502, 504 and an anterior surface 506 that extends in front of at least a portion of the cut distal end 12 of the femur 10. As discussed above, the trial implant 500 can couple to the reamer 320C, 320E in any suitable manner (e.g., using screws, a spline connection, tapered connection, cement, slot and key connection, press-fit connection, etc.).

Figure 14:
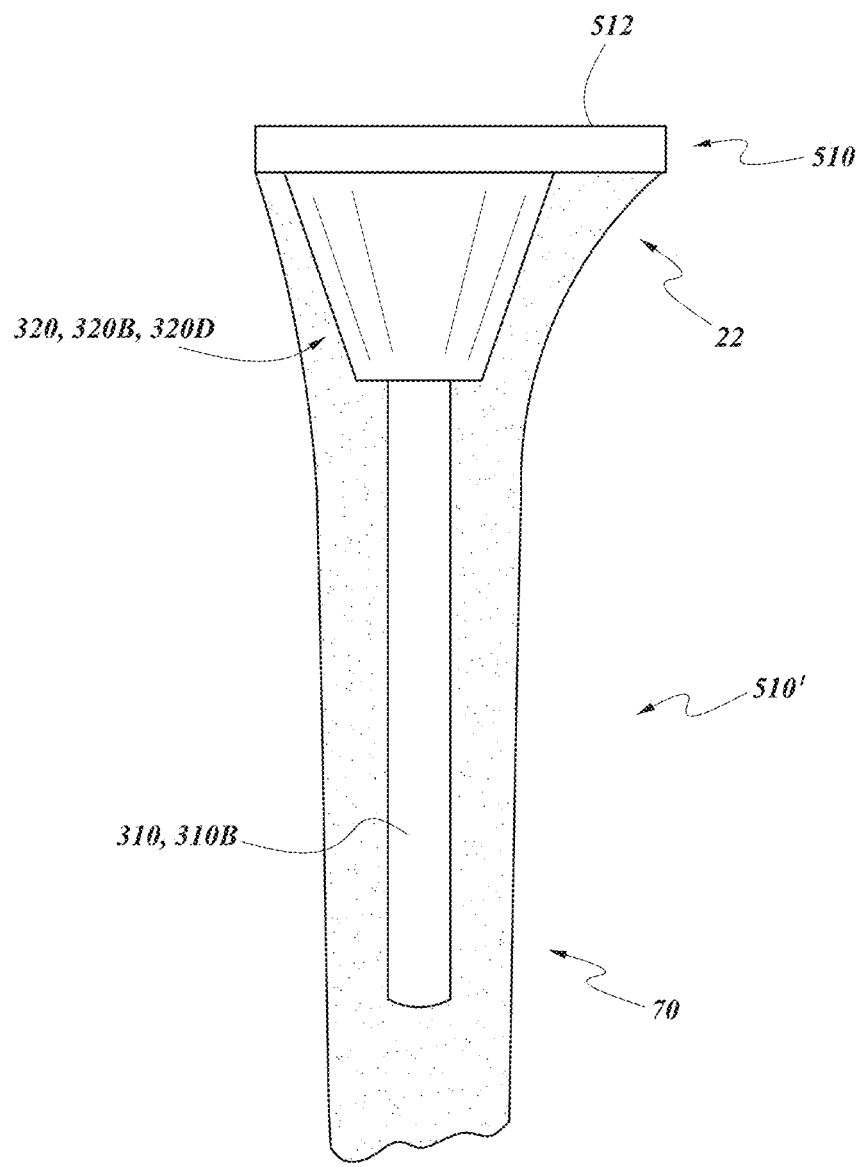
FIG. 14 is a schematic side view of a cut proximal end of the tibia bone with the reaming cone therein after installation of the trial tibial knee implant.

FIG. 14 shows a schematic front view of the distal end 22 of the tibia 20 with a trial implant assembly 510', which includes a trial implant 510, the reamer 320A, 320B, 320D and the elongate shaft or stem 310, 310B. The trial implant 510 for the tibia 20 can extend over at least a portion of the cut proximal end 22 of the tibia 20 and can define an articulating surface 512 that can contact the condyle surfaces 502, 504 of the trial implant 500 of the femur 10. As discussed above, the trial implant 510 can couple to the reamer 320A, 320B, 320D in any suitable manner (e.g., using screws, a spline connection, a tapered connection, cement, slot and key connection, press-fit connection, etc.).

Figure 15:
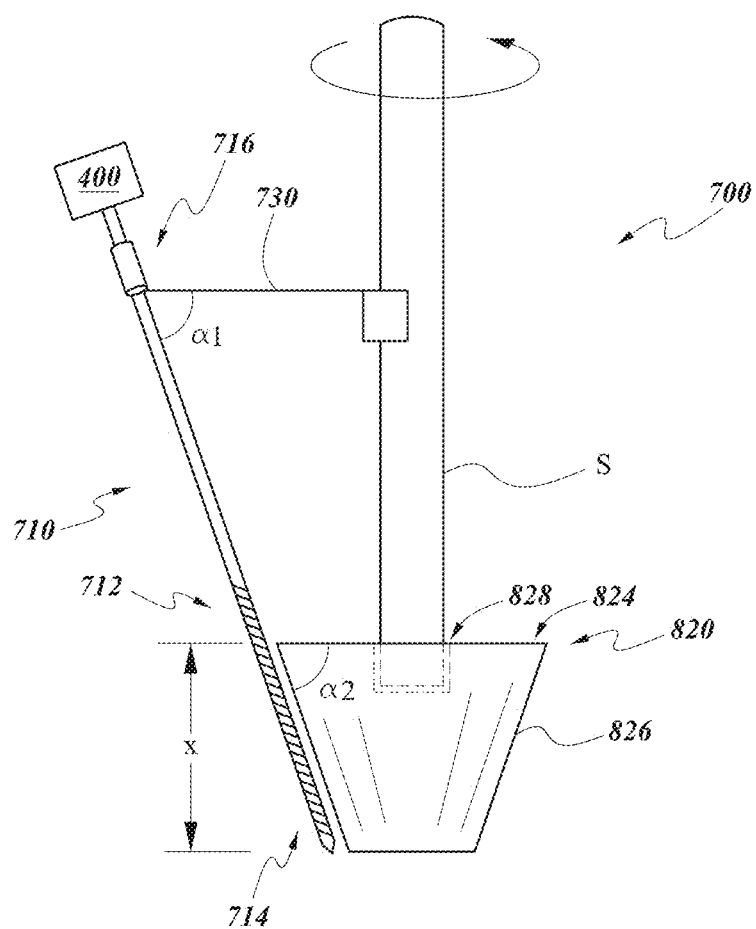
FIG. 15 is a schematic side view of a device for removing a knee implant.

FIG. 15 shows one embodiment of an assembly 700 for removing an implant assembly, as further discussed below. For simplicity, the elongate shaft and implant body, as well as the bone (e.g., femur 10, tibia 20) that the implant is located in is not shown in FIG. 15. The implant assembly includes a tapered cone body 820 similar in shape to the reamer 320A, 320B, 320D described above. In one embodiment, the tool 710 is a drill bit. In another embodiment, the tool 710 is a burr. In still another embodiment, the tool 710 is a router. The distal end 712 can have a length L that is at least as great as a height X of the tapered cone body 820. The tool 710 can be inserted between the outer surface 826 of the tapered cone body 820 and the bone, and the tool 710 can be operated (e.g., rotated about its axis) to detach or pry loose the tapered cone body 820 from the bone.

With continued reference to FIG. 15, the tool 710 can be inserted at an angle α1 that substantially coincides (e.g., is identical to) the angle α2 of the tapered cone body 820. A proximal end 716 of the tool 710 can be supported at the angle a1 by a support 730 that connects the tool 710 to a shaft S attached to a proximal end 824 of the tapered cone body 820 by a connector 828. The tool 710 can optionally be operated manually. In another embodiment, the tool 710 can be operated by a power tool such as a drill 410 that couples to the proximal end 716 of the tool 710.

Though FIG. 15 shows a tapered cone body 820 that is generally similar in size and shape with the reamer 320A, 320B, 320D, the implant assembly can instead have a tapered cone body with a cutout 820' that is similar in size and shape as the reamer 320C, 320E described above.

Figure 16:
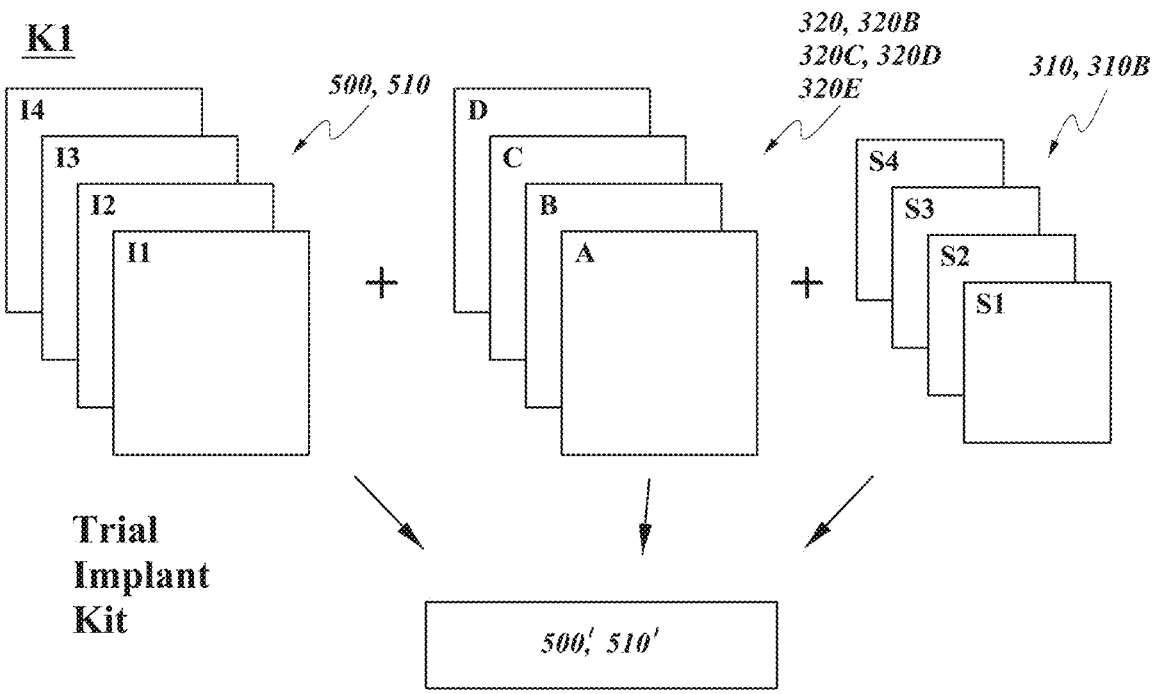
FIG. 16 is a schematic block diagram of a kit for a trial implant assembly and kit for a final implant assembly.
Figure 16:
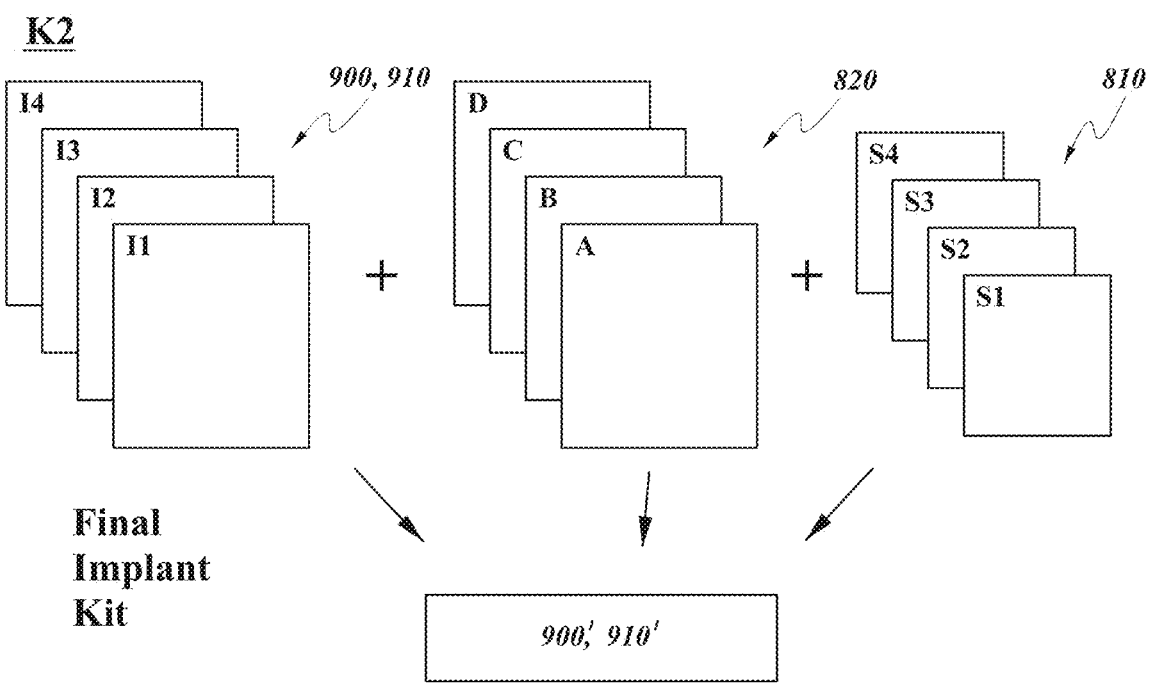

FIG. 16 shows an embodiment of a kit K1 for assembling a tibial trial implant assembly 510' and a femoral trial implant assembly 500'. The kit K1 can include a plurality of elongate members 310, 310B of various sizes S1-S4, a plurality of tapered cone reamers 320-320E of different sizes A-D, and a plurality of tibial trial implants 510 and femoral trial implants 500 of different sizes I1-I4. The surgeon would utilize the kit K1 to assemble the desired trial implant assembly 500', 510' for the femur and tibia, using different sized components, as needed to achieve the desired fit for the trail implant, as described further below in connection with FIG. 17. Once the surgeon obtained the desired trial implant assembly 500', 510', the surgeon could then assemble the final implant assemblies 900', 910' for the femur and tibia utilizing a similar kit K2 with similarly sized components for the elongate shaft 810, tapered cone body 820 and implant 900,910. Accordingly the different sizes of the components of the trial implant assembly 500, 510' correlate with the different sizes of the components of the final implant assembly 900, 910', simplifying the process of assembling the final implant assembly based on the trial implant assembly 500, 510' the surgeon determined was the appropriate one for the patient.

Figure 17:
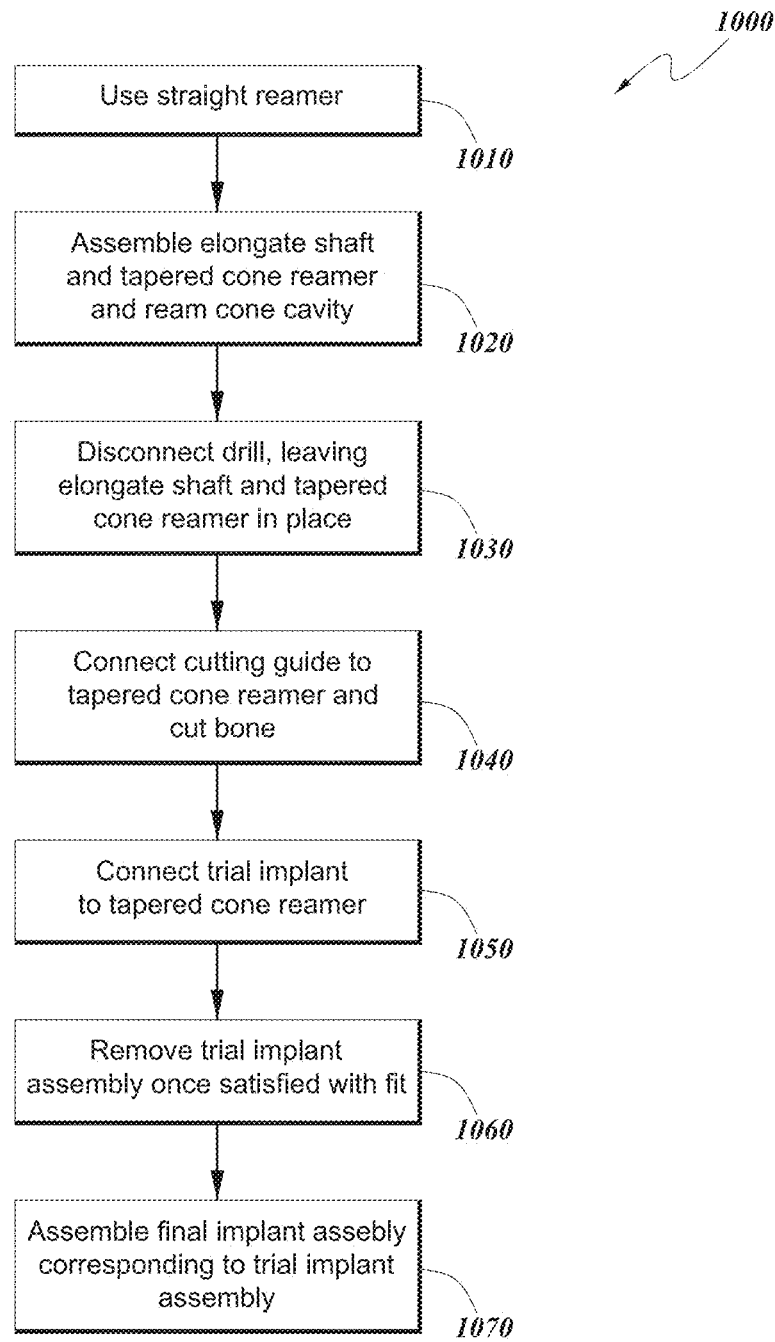
FIG. 17 is a block diagram showing a method of installing a knee implant.

FIG. 17 is a block diagram of a method 1000 of installing a total knee implant. The knee implant can include a femoral implant assembly 900 and a tibial implant assembly 910 that are implanted into the distal femur and the proximal tibia, respectively. The process below is described with respect to implanting the tibial implant assembly 910 on the tibia 20. However, a similar process is used to implant the femoral implant assembly 910, except that the tapered cone reamer with the cutout 320C, 320E is used, and a similarly shaped tapered cone body 820' is implanted once the trial implant assembly is removed.

At block 1010, the surgeon could use a straight reamer to ream a straight cavity in the bone (e.g., the tibia 20 or femur) and then it is taken out. If the straight reamer does not point at the ankle for the tibial implant or hip for the femoral implant (e.g., has an offset of 1 to 12 degrees from vertical), the surgeon would utilize a 1 to 12 degree adapter with the straight reamer to orient the proximal tibia to the ankle or distal femur to the hip.

At block 1020, the surgeon assembles the elongate shaft 310, 310B to the reamer 320A, 320B, 320D and inserts it into the straight cavity formed by the straight reamer. The elongate shaft 310, 310B provides angular orientation, while the reamer 320A, 320B, 320D provides rotational and axial stability (e.g., via the ridges 327A, 327B, 327D on its outer surface 326A, 326B, 326D). The elongate shaft 310 in one embodiment has a smaller outer diameter (e.g., 1-2 mm smaller) than the straight reamer to ensure the elongate shaft 310 is easily delivered into the straight cavity (e.g., does not get caught in the bone during insertion). The surgeon then proceeds to ream the proximal end 22 of the tibia 20 to ream the tapered cone shape cavity so that it points perpendicular to the ankle, or ream the distal end 12 of the femur 10 to ream the tapered cone shape cavity so that it points substantially perpendicular to the hip. The surgeon would continue to ream the cavity in the tibia 20 or femur until the desired size cavity was obtained (e.g., when sufficient boney opposition and cortical contact is obtained). For example, if using the modular reamer 320D, the surgeon can continue to sequentially nest reamer portions A-D of increasing size to obtain a larger tapered cone reamer body and form a larger tapered cone cavity in the tibia 20. As discussed above, the proximal end of the reamer 310A, 310B, 310D can be coupled to a shaft that is chucked to a drill 400, which can be operated to rotate the reamer 310A, 310B, 310D, without rotating the elongate shaft 310, 310B due to the rotatable (e.g., bearing) connection between the elongate shaft 310, 310B, 310D and the reamer.

At block 1030, the surgeon can disconnect the drill 400 from the proximal end 324A, 324B, 324C of the reamer 320A, 320B, 320D once the desired tapered cavity is achieved in the tibia 20, leaving the elongate shaft 310, 310B and the reamer 320A, 320B, 320D in place in the tibia 20.

At block 1040, the surgeon can connect a cutting guide 600 to the reamer 320A, 320B, 320D and cut the tibia 20 flush to the proximal end 324A, 324B, 324D of the reamer 320A, 320B, 320D.

At block 1050, the surgeon can disconnect the cutting guide 600 from the reamer 320A, 320B, 320D and connect the tibial trial implant 510 to define the trial implant assembly 510'. The surgeon would then determine if the trial implant assembly 510' meets his or her requirements for the tibial portion of the knee implant or requires further changes (e.g., requires a larger sized trial tibial implant 510). For example, the position and size of the trial implant assembly 510' can be adjusted until a well-balanced knee joint is achieved.

At block 1060, once the surgeon determines that the tibial trial implant assembly 510' meets the requirements for the tibial portion of the knee implant, the surgeon would remove the trial implant assembly 510' (e.g., the tibial trial implant 510, reamer 320A, 320B, 32D and elongate shaft 310, 310B) from the tibia 20.

At block 1070, the surgeon would assemble the final tibial implant assembly 910', which would have an elongate shaft 810, a tapered cone 820, and a tibial implant 910. The final tibial implant assembly 910' can be assembled in multiple pieces but is inserted into the cavity in the tibia 20 in one piece. The elongate shaft 810 would provide axial stability, while the tapered fluted or porous cone 820 can provide rotational stability (e.g., via one or more ridges that engage the bone in the cavity, such as the diaphysis).

The final tibial implant assembly 910' is similar (e.g. identical) in shape and size as the tibial trial implant assembly 510'. For example, the elongate shaft 810 can be similar (e.g. identical) in size and shape to the elongate shaft 310, 310B. Similarly, the tapered cone 820 can be similar (e.g. identical) in shape and size as the reamer 320A, 320B, 320C. Finally, the tibial implant 910 can be similar (e.g., identical) in size and shape as the trial tibial implant 510. The final tibial implant assembly 910' can differ from the tibial trial implant assembly 510' in the quality of the materials used. The surgeon can fix the final implant assembly 910' in the tibia 20 utilizing any suitable method (e.g., cementing the implant assembly 910' in the bone).

Advantageously, the size of each of the elongate shaft 310, 310B, the reamer 320A, 320B, 320D and the tibial implant 510 correspond to similarly sized elongate shaft 810, tapered cone 820 and tibial implant 910. Moreover, the elongate shaft 310, 310B, reamer 320A, 320B, 320D and tibial implant 510 can be provided in multiple sizes, allowing the surgeon to assembly a trial implant assembly 510' with different sized components to achieve the desired operation from the trial implant assembly 510'. Accordingly, utilizing the trial implant assembly 510' to determine the desired implant arrangement simplifies the implantation process as the surgeon can then assemble the final implant with a similarly sized elongate shaft, tapered cone and implant body as the trial implant assembly 510'.

Though the method 1000 described in the steps of FIG. 16 has been described with respect to the tibial implant assembly 910' one or skill in the art will recognize that substantially the same process can be used for the implantation of the femoral implant assembly 900'. However, for the femoral implant, the reamer 320C, 320E is used instead of the reamer 320A, 320B, 320D to provide the cutout 321C, 321E to accommodate the femoral trial implant 500 thereon, as previously described.

Figure 18:
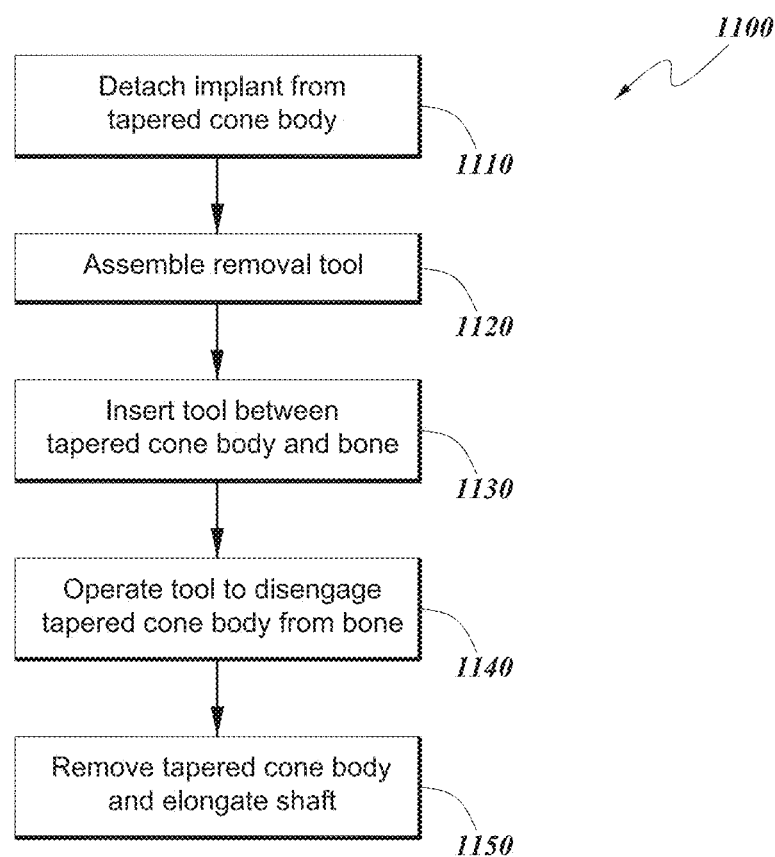
FIG. 18 is a block diagram showing a method of removing a knee implant.

FIG. 18 shows one embodiment of a method 1100 for removing a pre-existing implant assembly. To simplify the description, the method 1100 will be described for the removal of a previously implanted tibial implant assembly 910' having a shape and size as described herein. However, one of skill in the art will recognize that a substantially similar process can be utilized to remove a previously implanted femoral implant assembly 900' having a shape and size as described herein.

At step 1110, the surgeon could decouple the tibial implant 910 from the tapered cone 820.

At step 1120, the surgeon could attach the tool 710 of the removal assembly 700 to a shaft S and couple the shaft S to the tapered cone 820 so that the tool 710 extends at substantially the same angle as the angle of the tapered cone.

At step 1130, the surgeon could introduce the tool 710 between the outer surface 826 of the tapered cone 820 and the bone, as illustrated in FIG. 15.

At step 1140, the surgeon could operate the tool 710 (e.g. with a drill 400) and rotate the tool 710 about the circumference of the tapered cone 820 to disengage it from the bone about its periphery.

At step 1150, the surgeon could remove the tapered cone 820 and the elongate shaft 810 from the tibia 20, and proceed to prepare the cavity for the implantation of a new tibial implant assembly 910'.

Advantageously, because it is only the tapered cone 820 that provides rotational stability to the tibial implant assembly 910', is the portion of the implant assembly 910' that is rotationally fixed to the tibia, and sits at the proximal portion of the tibial implant assembly 910', the tool 710 does not need to be inserted to the distal end of the tibial implant assembly 910', but rather only needs to be extended to the distal end 822 of the tapered cone 820, which makes removal of the previously implanted tibial implant assembly 910' much easier and efficient to perform, and takes less time than if the rotational stability was also provided along a stem portion of the implant.

Accordingly, in the embodiments described herein, the height of the reamer 320-320E in the trial implant assembly 500', 510' and corresponding tapered cone 820 in the final implant assembly 900', 910' are the only portions that are rotationally fixed in the bone (femur 10, tibia 20). The elongate shaft 310, 310B in the trial implant assembly 500', 510' and elongate shaft 810 in the final implant assembly 900', 910' is not rotationally fixed in the bone (rather, it provides axial stability), so that the elongate shaft 310, 310B, 820 need not be dislodged from the bone by inserting a tool 710 to the distal end of the elongate shaft 310, 310B, 820. Accordingly, the tapered cone reamer 320-320E and tapered cone body 820 only define a proximal portion of the trial implant assembly 500',510' and final implant assembly 900', 910'. That is, the height or length of the tapered cone reamer 320-320E of the trial implant assembly 500', 510' and tapered cone body 820 of the final implant assembly 900', 910' provide a relatively small amount to the length of the trial implant assembly 500', 510' and final implant assembly 900', 910' relative to the length of the other components (e.g., elongate shaft 310, 310B, 810). In one embodiment, the height or length of the tapered cone reamer 320-320E of the trial implant assembly 500',510' and tapered cone body 820 of the final implant assembly 900', 910' is less than ½ the length of the trial implant assembly 500', 510' and final implant assembly 900', 910', respectively. In another embodiment, the height or length of the tapered cone reamer 320-320E of the trial implant assembly 500',510' and tapered cone body 820 of the final implant assembly 900', 910' is less than ⅓ the length of the trial implant assembly 500', 510' and final implant assembly 900', 910', respectively. In still another embodiment, the height or length of the tapered cone reamer 320-320E of the trial implant assembly 500',510' and tapered cone body 820 of the final implant assembly 900', 910' is less than ¼ the length of the trial implant assembly 500', 510' and final implant assembly 900', 910', respectively.

While certain embodiments of the inventions have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. For example, one portion of one of the embodiments described herein can be substituted for another portion in another embodiment described herein. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a sub combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A method for removing an implant assembly, the method comprising:
   mechanically supporting a tool relative to the implant assembly so that the tool is oriented at a fixed angle corresponding to an angle defined by an outer surface of an implant body fixed in a bone;
   linearly advancing the tool relative to the implant about an entire periphery of the implant to introduce at least a portion of the tool into an interface between the the outer surface of the implant body and the bone to detach the implant body from the bone; and
   removing the implant assembly from the bone.

2. The method of claim 1, wherein the tool is maintained at the angle while linearly advancing the tool relative to the implant.

3. The method of claim 1, further comprising rotating the tool about the at least a portion of the outer surface of the implant body while in the interface to disengage the implant assembly from the bone.

4. The method of claim 1, wherein the implant body comprises a tapered body.

5. The method of claim 4, wherein the tapered body comprises a tapered cone body.

6. The method of claim 5, wherein the tool is a burr.

7. The method of claim 1, wherein the tool is a drill bit.

8. The method of claim 1, wherein the tool is a router.

9. The method of claim 1, wherein the tool comprises a length of at least as great as a height of the implant body.

10. A removal assembly for removing an implant assembly, the removal assembly comprising:
    one or more tools, each tool comprising a proximal end and a distal end, the distal end configured to be inserted between at least a portion of an outer surface of the implant assembly and a bone; and
    a support configured to position and advance the one or more tools at a fixed predetermined angle aligned with an angle of the the outer surface of the implant assembly to allow the tool to be introduced about an entire periphery of the implant assembly within an interface between the outer surface of the implant assembly and the bone.

11. The removal assembly of claim 10, the support further configured to rotate the tool about a longitudinal axis of the tool while the support maintains the tool in a fixed position at the predetermined angle.

12. The removal assembly of claim 10, wherein the implant body comprises a tapered body.

13. The removal assembly of claim 12, wherein the tapered body comprises a tapered cone body.

14. The removal assembly of claim 10, wherein the tool is a burr.

15. The removal assembly of claim 10, wherein the tool is a drill bit.

16. The removal assembly of claim 10, wherein the tool is a router.

17. The removal assembly of claim 10, wherein the tool comprises a length of at least as great as a height of the implant body.

18. A removal assembly for removing an implant assembly, the removal assembly comprising:
    an tool comprising a proximal end and a distal end, the distal end configured to be inserted between an outer surface of the implant assembly and a bone; and
    a support that extends between a first end and a second end, the support being attached at the first end to the proximal end of the tool, the support being attached at the second end to a portion of the implant assembly, wherein the support allows the tool to rotate about a longitudinal axis of the tool and about an entire periphery of the implant assembly while the tool remains in a substantially fixed angular orientation,
    wherein the substantially fixed angular orientation is aligned with an angle of the outer surface of the implant assembly.

19. The removal assembly of claim 18, wherein the implant body comprises a tapered body.

20. The removal assembly of claim 19, wherein the tapered body comprises a tapered cone body.

21. The removal assembly of claim 18, wherein the tool comprises a length of at least as great as a height of the implant body.

* * * * *

UNITED STATES PATENT AND TRADEMARK OFFICE
CERTIFICATE OF CORRECTION

| | |
|---|---|
| PATENT NO. | : 11,344,320 B2 |
| APPLICATION NO. | : 16/833194 |
| DATED | : May 31, 2022 |
| INVENTOR(S) | : Derek Amanatullah |

It is certified that error appears in the above-identified patent and that said Letters Patent is hereby corrected as shown below:

In the Drawings

On Sheet 14 of 15 (Reference Numeral 1070, FIG. 17) at Line 1, delete "assebly" and insert --assembly--.

In the Specification

In Column 3 at Line 27, delete "6A" and insert --6A.--.

In Column 9 at Line 54, delete "a1" and insert --$\alpha$1--.

In Column 13 at Lines 58-59, delete "sub combination." and insert --subcombination.--.

In the Claims

In Column 15 at Line 14, in Claim 1, delete "the the" and insert --the--.

In Column 15 at approximately Line 42, in Claim 10, delete "the the" and insert --the--.

Signed and Sealed this
Thirtieth Day of August, 2022

Katherine Kelly Vidal
*Director of the United States Patent and Trademark Office*